United States Patent
Cheng et al.

(10) Patent No.: US 11,926,697 B2
(45) Date of Patent: Mar. 12, 2024

(54) FLUORINE-CONTAINING LIQUID CRYSTAL ELASTOMER AND PREPARATION METHOD AND USE THEREOF

(71) Applicant: SOOCHOW UNIVERSITY, Suzhou (CN)

(72) Inventors: Zhenping Cheng, Suzhou (CN); Kai Tu, Suzhou (CN); Enjie He, Suzhou (CN); Jiannan Cheng, Suzhou (CN); Lifen Zhang, Suzhou (CN); Xiulin Zhu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 513 days.

(21) Appl. No.: 17/270,593

(22) PCT Filed: Aug. 20, 2020

(86) PCT No.: PCT/CN2020/110117
§ 371 (c)(1),
(2) Date: Feb. 23, 2021

(87) PCT Pub. No.: WO2021/155660
PCT Pub. Date: Aug. 12, 2021

(65) Prior Publication Data
US 2022/0119589 A1    Apr. 21, 2022

(30) Foreign Application Priority Data
Feb. 7, 2020   (CN) .......................... 202010082606.X

(51) Int. Cl.
| | | |
|---|---|---|
| C08G 61/12 | (2006.01) | |
| B29C 55/00 | (2006.01) | |
| B29C 55/04 | (2006.01) | |
| C07C 227/16 | (2006.01) | |
| C08J 5/18 | (2006.01) | |
| C09K 19/38 | (2006.01) | |
| F04B 49/00 | (2006.01) | |
| G08C 23/04 | (2006.01) | |
| B29K 105/00 | (2006.01) | |
| B29L 7/00 | (2006.01) | |

(52) U.S. Cl.
CPC .......... *C08G 61/121* (2013.01); *B29C 55/005* (2013.01); *B29C 55/04* (2013.01); *C07C 227/16* (2013.01); *C08J 5/18* (2013.01); *C09K 19/3804* (2013.01); *F04B 49/00* (2013.01); *G08C 23/04* (2013.01); *B29K 2105/0079* (2013.01); *B29L 2007/008* (2013.01); *C08G 2261/124* (2013.01); *C08G 2261/316* (2013.01); *C08G 2261/53* (2013.01); *C08G 2261/76* (2013.01); *C08J 2365/00* (2013.01)

(58) Field of Classification Search
CPC   C09K 19/38; C09K 19/3804; C09K 19/0444; C09K 19/0448; C08G 61/121; C08G 2261/124; C08G 2261/316; C08G 2261/53; C08G 2261/76; C08J 2365/00
See application file for complete search history.

(56) References Cited

U.S. PATENT DOCUMENTS

2022/0119589 A1*   4/2022   Cheng .................. C08J 5/18

FOREIGN PATENT DOCUMENTS

| CN | 103524678 A | 1/2014 |
| CN | 105482013 A | 4/2016 |
| CN | 107619466 A | 1/2018 |
| CN | 111253510 A | 6/2020 |
| DE | 10004442 A1 | 9/2000 |

OTHER PUBLICATIONS

Donnio et al., A Simple and Versatile Synthetic Route for the Preparation of Main-Chain, Liquid-Crystalline Elastomers, Macromolecules, 2000, 33, 7724-7729 (Dec. 31, 2000).

* cited by examiner

*Primary Examiner* — Geraldina Visconti
(74) *Attorney, Agent, or Firm* — SZDC Law PC

(57) ABSTRACT

The present invention provides a fluorine-containing liquid crystal polymer of Formula (1). The present invention also discloses a fluorine-containing liquid crystal elastomer, which comprises a copolymer of a fluorine-containing liquid crystal polymer of Formula (1) with a near-infrared dye of Formula (2). The fluorine-containing liquid crystal elastomer of the present invention shrinks due to the photothermal conversion effect of the material under the irradiation of near-infrared light, and thus is widely applicable to the field of actuators. The fluorine-containing liquid crystal polymer of the present invention introduces fluorine-containing segments into the cross-linked network of the liquid crystal polymer, to improve the mechanical performance of the material, and greatly extend the service time of light-controlled actuators.

4 Claims, 10 Drawing Sheets

FLUORINE-CONTAINING LIQUID CRYSTAL ELASTOMER AND PREPARATION METHOD AND USE THEREOF

This application is the National Stage Application of PCT/CN2020/110117, filed on Aug. 20, 2020, which claims priority to Chinese Patent Application No. 202010082606.X, filed on Feb. 7, 2020, which is incorporated by reference for all purposes as if fully set forth herein.

FIELD OF THE INVENTION

The present invention relates to the technical field of fluorine-containing liquid crystal elastomers and liquid transport, and more particularly to a fluorine-containing liquid crystal elastomer and a preparation method and use thereof.

DESCRIPTION OF THE RELATED ART

In recent years, as a new type of stimulus pattern, light has unique advantages such as remote operability, instantaneity, and precise control, and thus stands out from many traditional stimulus patterns. Therefore, soft actuators based on light response have gradually become a major research hotspot in the kingdom of science, and corresponding light-responsive polymers emerge accordingly. As early as in the last century, pioneer reports on light-responsive polymer materials are available. Researchers have found that amorphous polymers containing azobenzene can shrink by 1% under light irradiation. After decades of constant efforts by researchers, it has been discovered that ordered liquid crystal polymers have the characteristics of entropy elasticity and reversible deformation, and have promising application prospects in the preparation and design of soft actuators.

The first reported photodeformable cross-linked liquid crystal elastomer (*Phys. Rev. Lett.* 2001, 87, 015501.) can achieve a 20% shrinkage, but it is only limited to simple shrinkage and expansion. With continuous research and development, various more complex 3D actuation modes such as bending, twisting, and oscillation are gradually realized. The molecular structures and processing technologies of these liquid crystal elastomers are quite different, but their actuation principles mainly include reversible photochemical isomerization and photothermal effect. Reversible photochemical isomerization is mainly to achieve the macroscopic deformation of a material by taking advantage of the reversible photochemical isomerization of photoisomericmesogens in a liquid crystal polymer. The most typical representative material is azobenzene, which can achieve the interconversion between a rod-shaped trans-isomer and a curved cis-isomer under the irradiation of visible and ultraviolet light. Photothermal effect is to realize the interconversion between the isotropy and anisotropy of a liquid crystal elastomer by means of the temperature change in an illuminated area by adding a high-efficiency photothermal conversion molecule to a liquid crystal polymer.

Regardless of the actuation principles, the ultimate goal of studying photo-deformable liquid crystal elastomers is to produce corresponding light-controlled actuation devices to replace some dangerous manual operations or realize biomedical applications. So far, the reported light-responsive mechanical models of motion include micro-manipulators based on liquid crystal elastomers (*Nature* 2017, 546, 632), micro-motors (*Adv. Mater.* 2017, 29, 1606467), rollers (*Soft Matter* 2010, 6, 3447.), micro-robots (*Angew. Chem., Int. Ed.* 2008, 47, 4986.) and so on. In biomedical applications, the light-controlled microfluidic transport reported by Professor Yu Yanlei is a milestone (*Nature* 2016, 537, 179.). In summary, in the development of actuators in the past ten years, researchers are more preferable to study smaller-sized actuators. The size of actuators ranges from micrometers to nanometers, and their light response speed is relatively slow. However, in practical industrial applications, actuators with large size and fast and stable response that can implement a task without any manual operations are sought.

Professor Yang Hong recently reported a fast-response liquid crystal elastomer having a cross-linked backbone (*J. Am. Chem. Soc.* 2017, 139, 11333.), making it possible to attain a fast-response light-controlled "pump". However, the service durability of the liquid crystal elastomer having a cross-linked backbone needs to be improved.

CN201610063858.1, CN201710840585.1, and CN201910579630.1 disclose a polymerization method for preparing a fluorine-containing alternating copolymer by stepwise radical transfer-addition-termination under the irradiation of visible light, a polymerization method for preparing a fluorine-containing alternating polymer in the presence of a photocatalyst, and a photopolymerization method for preparing a block copolymer of an alternating copolymer with a "semi-fluorinated" backbone. The fluorine-containing alternating copolymers or the block copolymer of "semi-fluorinated" alternating copolymer prepared above do not have light-responsive behavior. It is necessary to develop a new fluorine-containing liquid crystal elastomer with good mechanical performance and light responsiveness.

SUMMARY OF THE INVENTION

To solve the above technical problems, an object of the present invention is to provide a fluorine-containing liquid crystal elastomer and a preparation method and use thereof. The present invention provides a fluorine-containing liquid crystal elastomer that is a light-responsive material. The material has good mechanical performance, shrinks under the irradiation of near-infrared light and can be used to prepare an actuator.

A fluorine-containing liquid crystal polymer of the present invention has a structure of Formula (1) below:

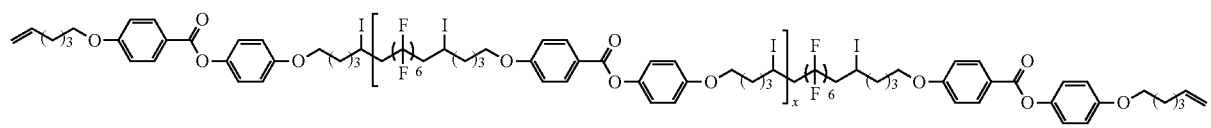

(1)

where X=5-12.

The present invention also provides a method for preparing a fluorine-containing liquid crystal polymer of Formula (1), which comprises the following steps:

in the absence of oxygen, reacting the compound of Formula 11 with 1,6-diiodoperfluorohexane in the presence of an organic photocatalyst and a promoter in an organic solvent under light irradiation, to obtain the fluorine-containing liquid crystal polymer of Formula (1) after the reaction is completed, where the compound of Formula 11 is shown below:

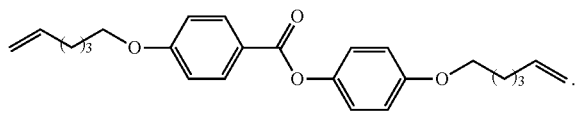

(11)

Preferably, the reaction temperature is 15-20° C., and the wavelength of light is 390-590 nm, more preferably 440-480 nm, and still more preferably 460 nm.

Preferably, the organic photocatalyst is tris(bipyridine) ruthenium chloride.

Preferably, the promoter is sodium ascorbate.

Preferably, the molar ratio of the compound of Formula 11 to 1,6-diiodoperfluorohexane is 1-1.4:1, and more preferably 1.2:1.

The present invention also provides a method for preparing a fluorine-containing liquid crystal elastomer, which comprises the following steps:

(1) under a protective atmosphere, reacting a fluorine-containing liquid crystal polymer of Formula (1) and a near-infrared dye of Formula (2) in the presence of Grubbs catalyst in an organic solvent at 58-65° C. (preferably 60° C.) for 1.5-2.5 hrs to obtain a preliminarily cross-linked polymer; and (2) applying an external force to the preliminarily cross-linked polymer, and allowing the preliminarily cross-linked polymer to react at 110-130° C. (preferably 120° C.) under the action of the external force, to obtain the fluorine-containing liquid crystal elastomer after the reaction is completed, where the compounds of Formulas (1)-(2) are shown below:

Preferably, in Step (1), the molar ratio of the fluorine-containing liquid crystal polymer to the near-infrared dye is 4:1-6:1.

Preferably, in Step (1), the preliminarily cross-linked polymer is in the shape of a film; and in Step (2), the external force is a tensile force, and the preliminarily cross-linked polymer in the shape of a film deforms along its length direction under the action of the external force.

The near-infrared dye molecules have particular absorption in the near-infrared band, and can convert the light energy into heat energy, thereby enabling the reversible macroscopic deformation of the material. In order to integrate the near-infrared dye molecules into the fluorine-containing liquid crystal elastomer, a near-infrared dye with a four-arm structure of Formula (2) is used in the present invention, which is referred to as NIR823, and synthesized through a specific synthesis route below:

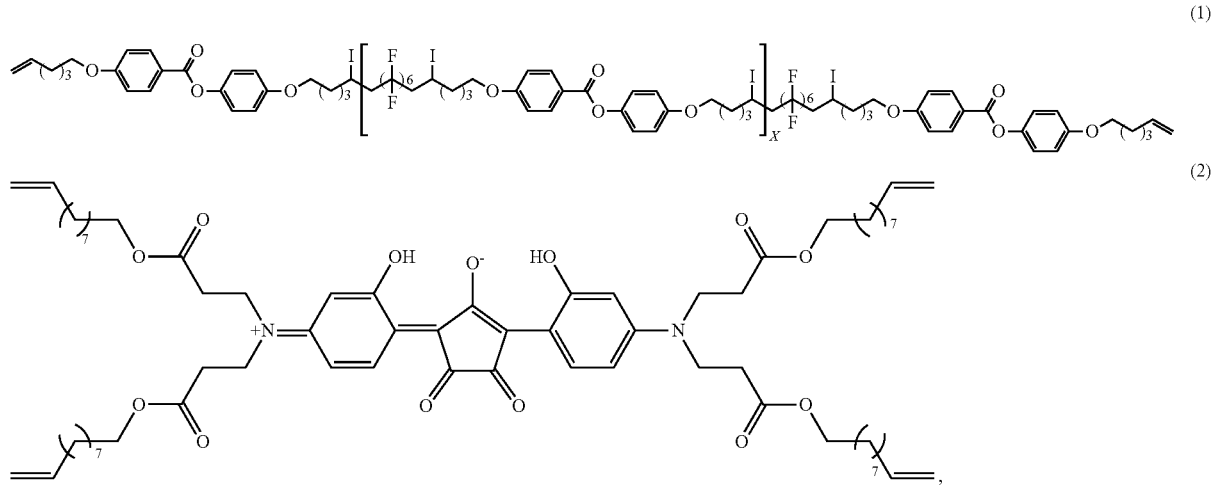

where X=5-12.

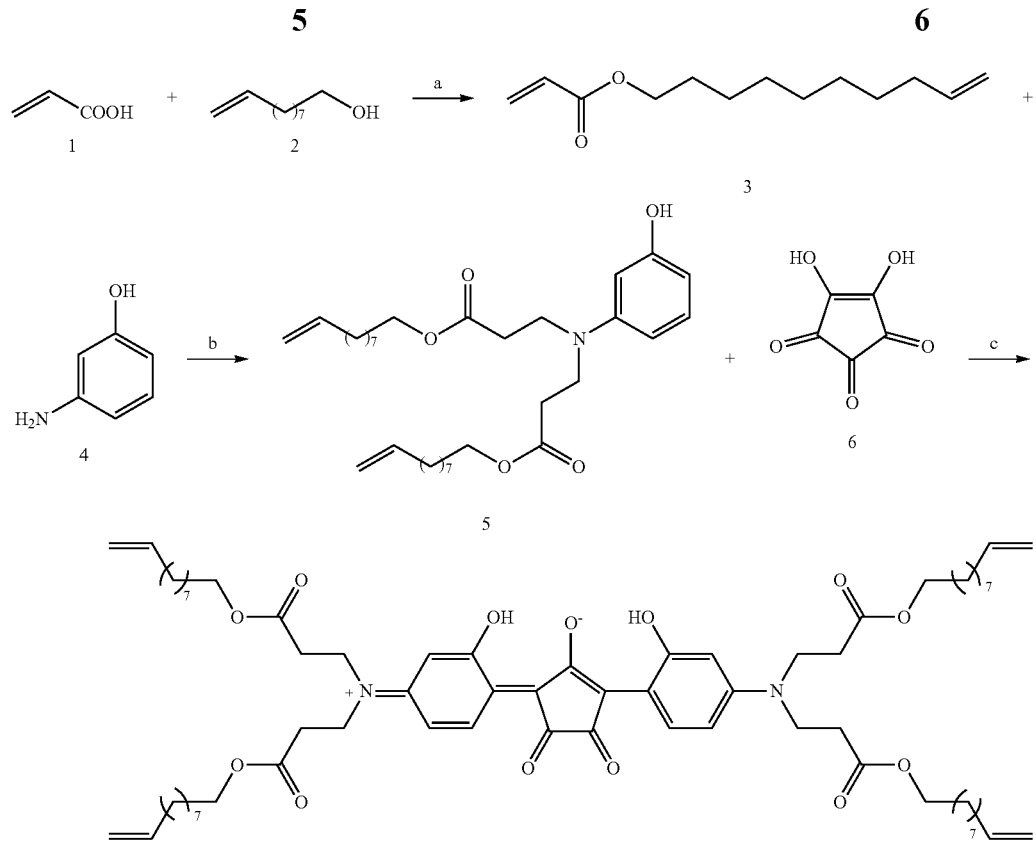

NIR823

The ultraviolet absorption spectrum shows that the maximum absorption peak of NIR823 is at 823 nm, which falls within the setting of near-infrared band. Further, under the action of external force, the preliminarily cross-linked polymer in the shape of a film is extended to 1.5-1.8 times the original length. By applying an external force, the preliminarily cross-linked polymer is further oriented, to obtain a fluorine-containing liquid crystal elastomer.

The fluorine-containing liquid crystal elastomer of the present invention is prepared by a new method of stepwise radical transfer-addition-termination polymerization. This polymerization method has the following three unique advantages. (1) A double bond at the end of the polymer chain is kept intact to serve as a reaction site for a cross-linked network. (2) Fluorine-containing segments are strictly alternately arranged in the polymer structure, which coincides with the alternating arrangement of rigid segments and flexible segments in the liquid crystal molecular structure. (3) The C—I bond generated during the polymerization process improves the solubility of the polymer in an organic solvent, which is beneficial to the preparation of the elastomer film.

It is to be noted that if the fluorine-containing liquid crystal polymer of Formula (1) does not contain a C—I bond, it cannot be dissolved in an organic solvent. Therefore, it fails to be polymerized with the near-infrared dye of Formula (2). Then, the fluorine-containing liquid crystal elastomer cannot be obtained. The present invention also claims a fluorine-containing liquid crystal elastomer prepared by the above method, which comprises a copolymer of a fluorine-containing liquid crystal polymer of Formula (1) with a near-infrared dye of Formula (2), where the copolymer in the fluorine-containing liquid crystal elastomer is oriented.

The present invention also discloses use of the fluorine-containing liquid crystal elastomer in a near-infrared light and/or thermally responsive actuator.

Preferably, the actuator is applicable to the preparation of manipulators, micro-motors, rollers, micro-robots, and liquid transport pumps, etc.

Preferably, the actuator responds to near-infrared light. Compared with light sources in other bands, near-infrared light has potentially a great application value due to its low energy and strong penetrating ability. Compared with thermally responsive materials, the irradiation area and response speed of light-responsive materials can be more easily controlled.

The present invention also discloses a near-infrared light-controlled liquid transport pump, which comprises a fluorine-containing liquid crystal elastomer of the present invention, a light source for generating near-infrared light and irradiating the fluorine-containing liquid crystal elastomer, and a liquid delivery pipe for liquid delivery. Two ends of the liquid delivery pipe are respectively in fluid communication with a first container and a second container, where the first container and the second container are used to hold a liquid. The liquid delivery pipe is also connected with a water storage unit, and the water storage unit is respectively in fluid communication with the first container and the second container. The water storage unit is provided with a piston rod therein, and the piston rod is connected with the fluorine-containing liquid crystal elastomer. A one-way valve (also called a check valve) is provided respectively between the first container and the water storage unit and between the second container and the water storage unit. By controlling the on or off of the light source, the fluorine-containing liquid crystal elastomer is allowed to shrink and recover to drive the piston rod to reciprocate, whereby the piston rod drives the liquid in the first container to enter the second container via the water storage unit.

Preferably, when the light source is turned on, the fluorine-containing liquid crystal elastomer shrinks and the piston rod is driven to move, so that the liquid in the first container is sucked into the water storage unit through the liquid delivery pipe. When the light source is turned off, the fluorine-containing liquid crystal elastomer gradually recovers to the original length, and the piston rod is driven to move, so that the liquid in the water storage unit is transported to the second container through the liquid delivery pipe. Because of the one-way valve provided respectively between the first container and the water storage unit and between the second container and the water storage unit, the liquid will not flow into the first container again.

Preferably, the water storage unit is a syringe.

By means of the above solution, the present invention has at least the following advantages.

In the present invention, a light-responsive fluorine-containing liquid crystal polymer is prepared, which is copolymerized with a near-infrared dye molecule to prepare a fluorine-containing liquid crystal elastomer that is a light-responsive material. The fluorine-containing liquid crystal elastomer shrinks due to the photothermal conversion effect of the material under the irradiation of near-infrared light, and thus can be widely used in the field of actuators. The fluorine-containing liquid crystal polymer of the present invention introduces fluorine-containing segments into the cross-linked network of the liquid crystal polymer, thus improving the mechanical performance of the material, and greatly extending the service time of light-controlled actuators.

In addition, based on the working principle of reciprocating piston pumps, the present invention also provides a high-efficiency near-infrared light-controlled liquid transport pump that is absolutely controlled by near-infrared light to realize liquid transport under control by light. The light-controlled "pump" can realize the fast, accurate and long-lasting light-controlled transport of liquids. In such a design, the light source used is near-infrared light, because compared to ultraviolet light sources, near-infrared light has a greater potential in use.

The above description is only a summary of the technical solutions of the present invention. To make the technical means of the present invention clearer and implementable in accordance with the disclosure of the specification, the preferred embodiments of the present invention will be described in detail with reference to the accompanying drawings.

LIST OF REFERENCE NUMERALS

1—fluorine-containing liquid crystal elastomer; 2—light source; 3—liquid delivery pipe; 4—first container; 5—second container; 6—one-way valve; 7—liquid in water storage unit; 8—water storage unit; 20—near-infrared light; 80—piston rod

DETAILED DESCRIPTION OF THE PREFERRED EMBODIMENTS

The specific embodiments of the present invention will be described in further detail with reference to embodiments. The following embodiments are intended to illustrate the present invention, instead of limiting the scope of the present invention.

Example 1: Synthesis of NIR823

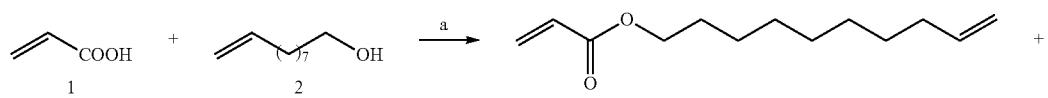

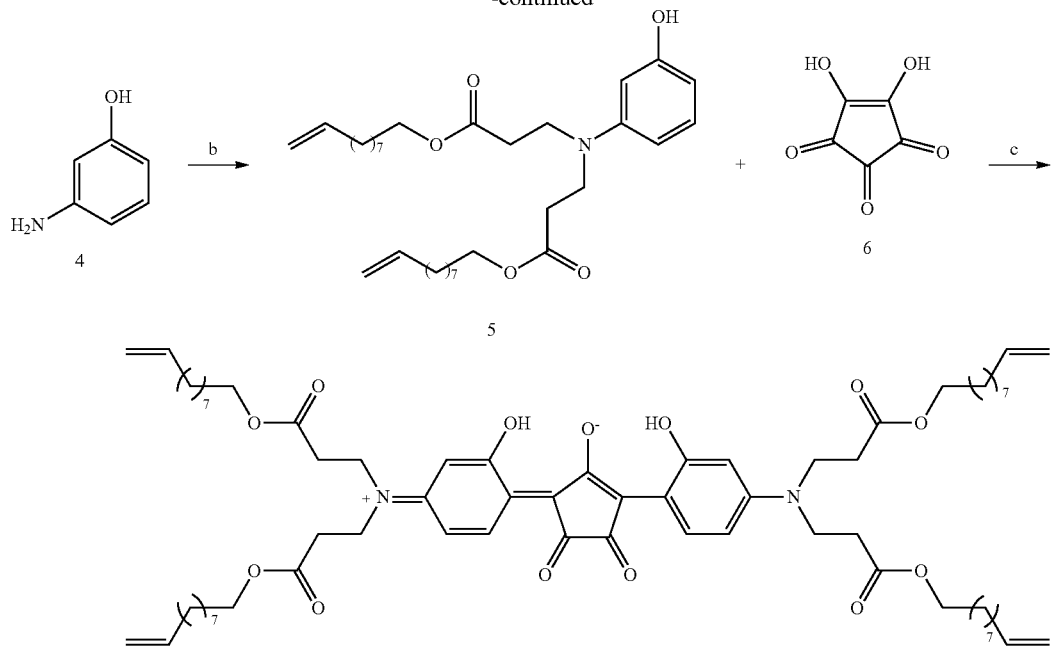

NIR823

Preparation of Compound 3: 3.60 g of acrylic acid, 7.80 g of 9-decen-1-ol, 0.61 g of 4-dimethylaminopyridine, and 9.60 g of 1-ethyl-(3-dimethylaminopropyl)carbodiimide hydrochloride, 13.90 ml of triethylamine and 150 ml of dichloromethane were sequentially added to a 250 mL three-neck round bottom flask. Under a nitrogen atmosphere, the reaction was stirred at room temperature for 12 h. After the reaction, the solvent was removed by a rotary evaporator. Subsequently, the crude product was purified by column chromatography (petroleum ether:ethyl acetate=4:1) to obtain Compound 3.

Preparation of Compound 5: To a 100 mL round bottom flask, 3.15 g of Compound 3, 545 mg of 3-aminophenol and 150 mL of acetic acid were sequentially added. The reaction mixture was stirred at 80° C. for 5 h. Subsequently, the crude product was purified by column chromatography (petroleum ether:ethyl acetate=4:1) to obtain Compound 5.

Preparation of NIR823: To a 100 mL round-bottom flask, 0.74 g of Compound 5, 100 mg of crotonic acid 6 and 15 ml of toluene were sequentially added. The whole reaction was carried out under a nitrogen atmosphere, and refluxed with stirring at 90° C. for 5 h. After the reaction, the solvent was removed by distillation under vacuum. The crude product was subsequently purified by column chromatography (petroleum ether:ethyl acetate=10:1) to obtain NIR823 as a black solid.

Figure 1:
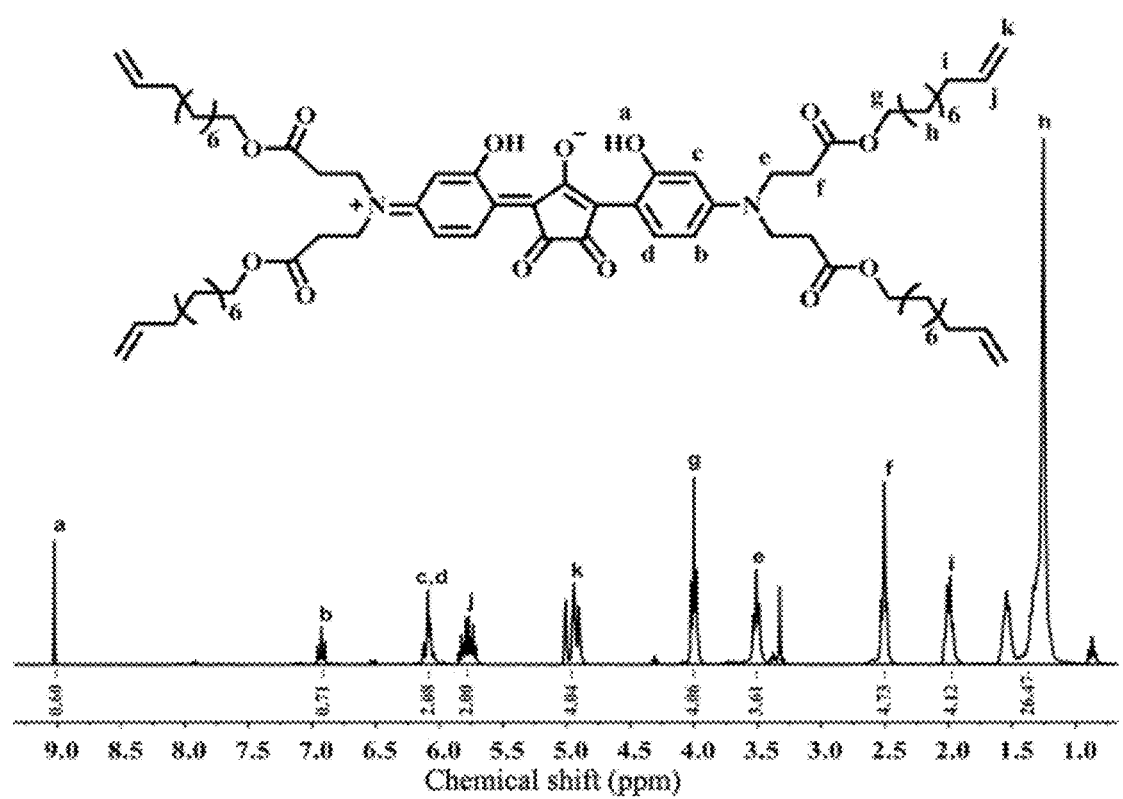
FIG. 1 is a $^1$H NMR spectrum of NIR823.

FIG. 1 is a NMR spectrum of NIR823 prepared by the above method.

Figure 2:
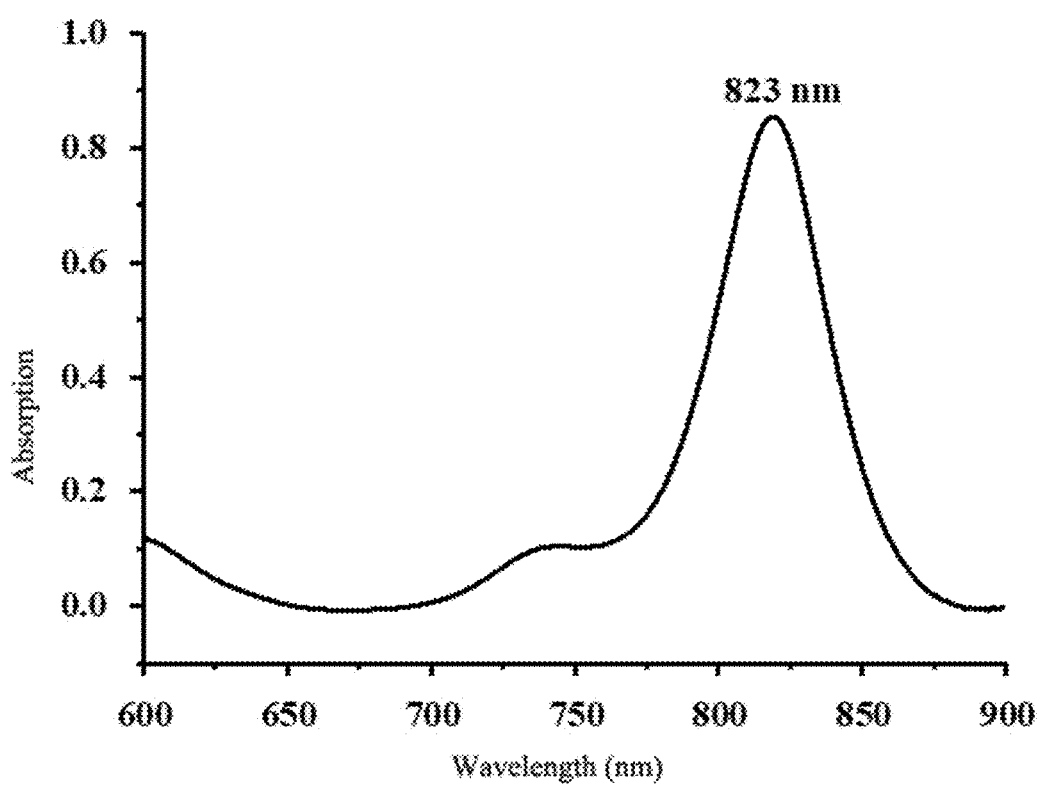
FIG. 2 is a UV absorption spectrum of NIR823.

FIG. 2 is a UV absorption spectrum of NIR823, in which the maximum absorption peak is at 823 nm in the near-infrared band.

Example 2: Preparation of Fluorine-Containing Liquid Crystal Polymer

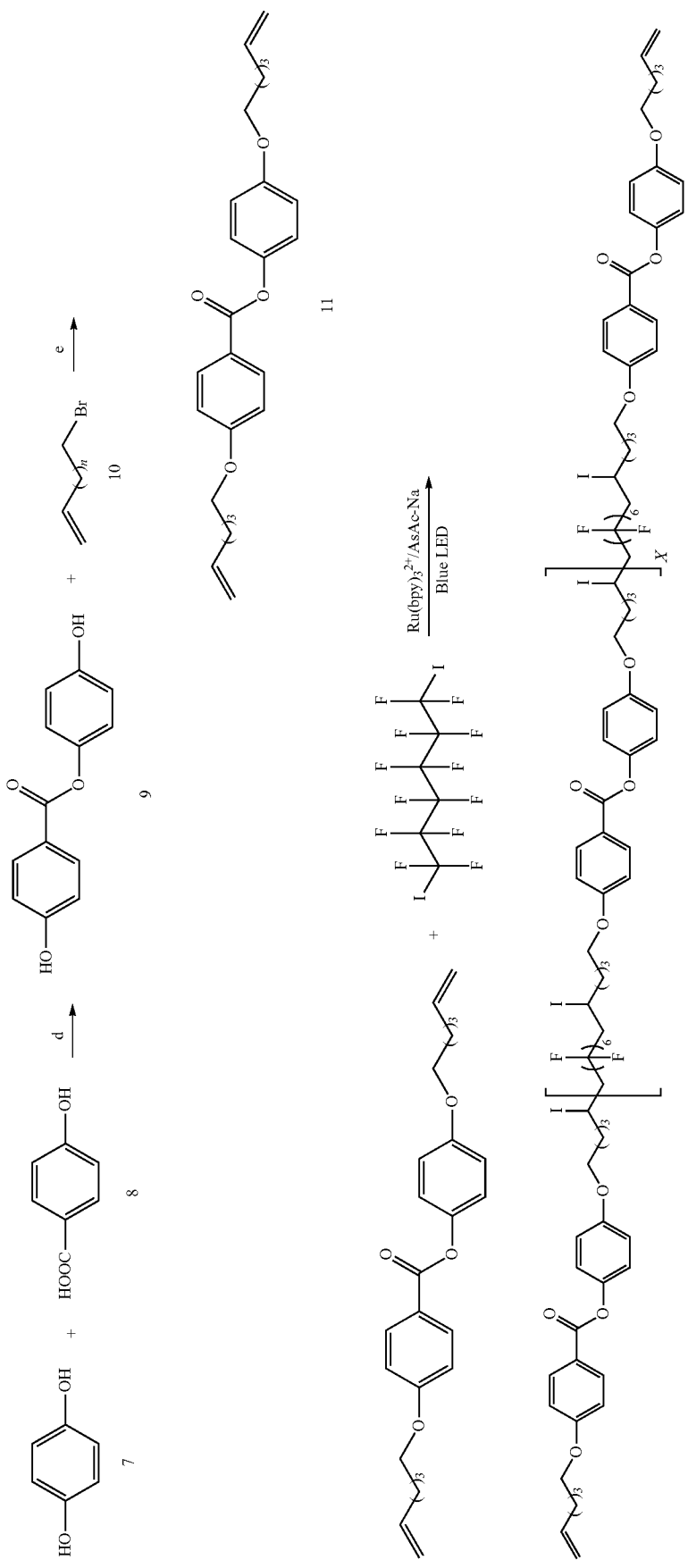

Preparation of Compound 9: 9.74 g of hydroquinone (Formula 7), 10 g of p-hydroxybenzoic acid (Formula 8), 0.35 g of boric acid, 0.5 ml of sulfuric acid, 10 ml of xylene and 40 ml of toluene were sequentially added to a 250 ml three-neck flask. The mixture was reacted under reflux at 137° C. for 5 h. After the reaction, the reaction solution was filtered under suction, the solvent was removed, and the solid product was washed with water until it was colorless. The product could be directly used in the next reaction.

Preparation of Compound 11: 4.60 g of Compound 9, 13.8 g of potassium carbonate, 6.52 g of 6-bromo-1-hexene and 100 ml of acetonitrile were sequentially added to a 250 ml three-neck flask. The reaction was refluxed at 90° C. for 5 h. After the reaction was completed, potassium carbonate was removed by suction filtration. The crude product was separated by column chromatography (petroleum ether:ethyl acetate=4:1) to obtain Compound 11 as a white solid.

Polymerization operation: 2.37 g of Compound 11, 2.77 g of 1,6-diiodododecafluorohexane, 0.495 g of sodium ascorbate and 0.064 g of tris(bipyridine)ruthenium chloride were sequentially added to a 25 ml Schlenk tube. A mixed solvent of 6 ml of 1,4-dioxane and 2 ml of methanol was used. The reaction mixture was degassed by at least four freezing-pumping-thawing cycles to completely remove dissolved oxygen, and then the Schlenk tube was irradiated with blue LED light with stirring at room temperature. The light wavelength is adjustable within 390-590 nm. After reaction for 12 h, the product was dissolved in 3 ml of tetrahydrofuran and then dripped into 250 ml of methanol to precipitate out. Finally, unreacted small molecules were removed by extraction with methanol for 48 h, to obtain a fluorine-containing polymer (designated as CFCI666).

Figure 3:
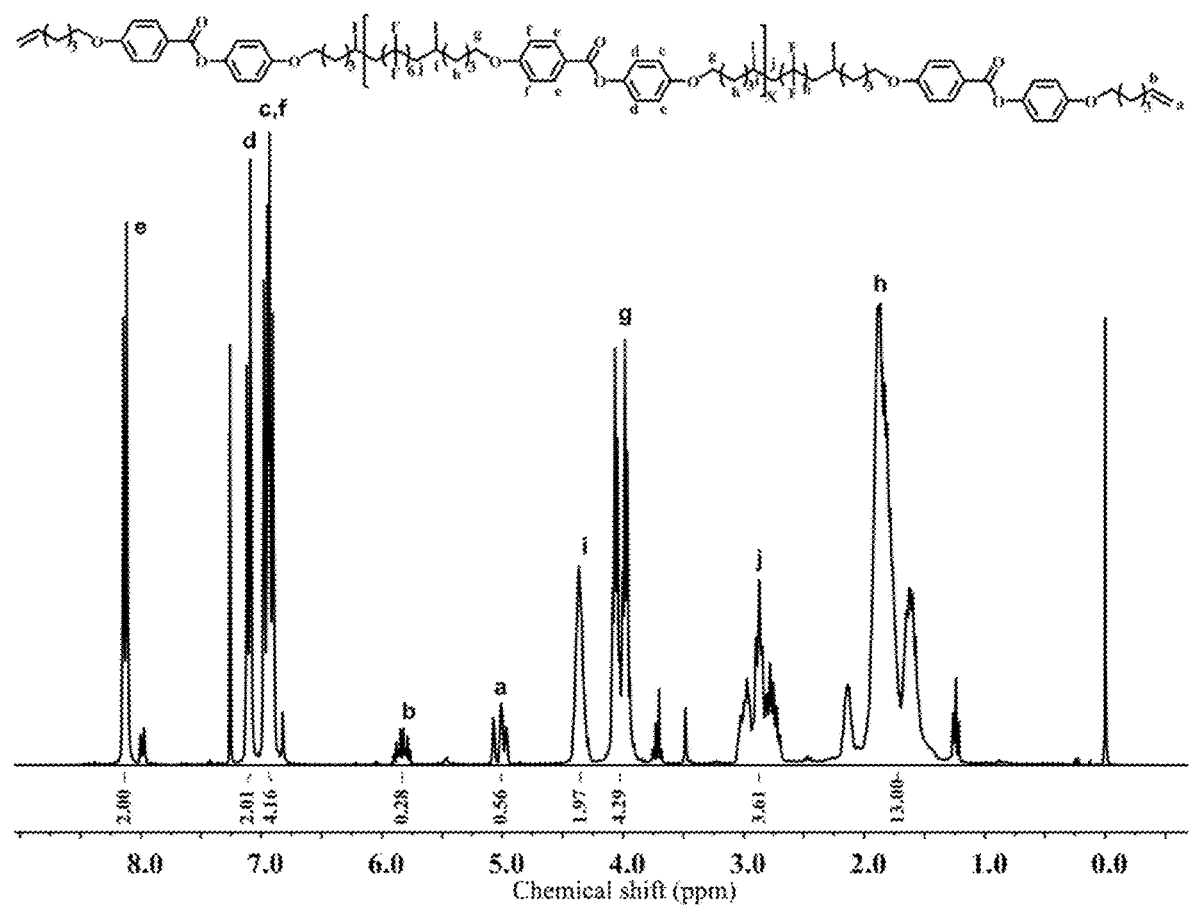
FIG. 3 is a $^1$H NMR spectrum of the fluorine-containing liquid crystal polymer CFCI666.

FIG. 3 is a $^1$H NMR spectrum of the fluorine-containing polymer CFCI666 prepared by the above method.

Figure 4:
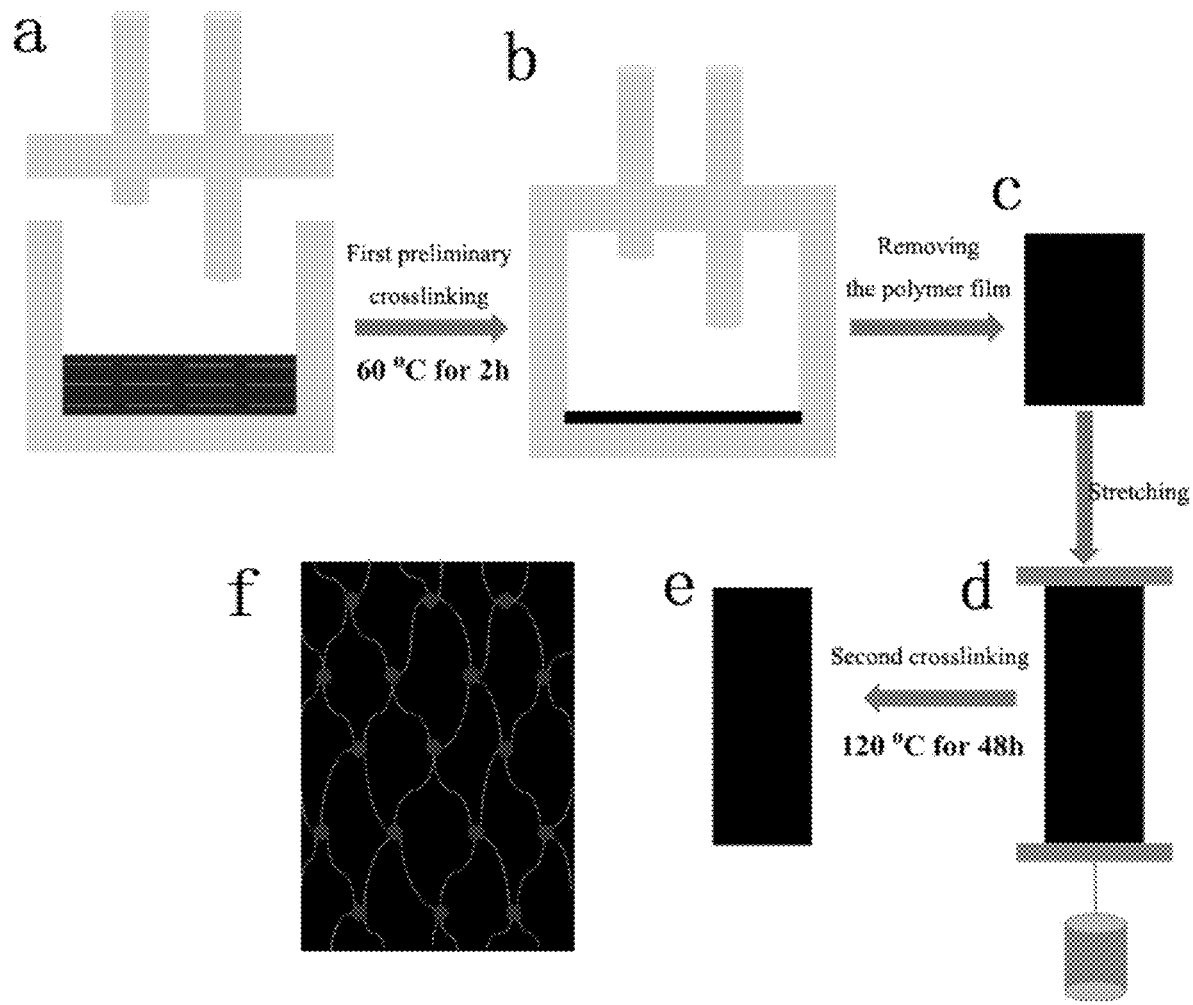
FIG. 4 is a flow chart of a process for preparing a fluorine-containing liquid crystal elastomer.

Example 3: Preparation of Fluorine-Containing Liquid Crystal Elastomer 30 mg of NIR823, 300 mg of CFCI666 and 6 mg of Grubbs catalyst 2nd-Generation were dissolved in 2 ml of toluene and ultrasonicated for 2 min. The solution was poured into a customized polytetrafluoroethylene mold (FIG. 4a), heated to 60° C. under a nitrogen atmosphere, and reacted for 2 h. The mold was cooled to room temperature and the polymer film (FIGS. 4B-c) was removed to complete the first preliminary crosslinking and obtain a preliminarily crosslinked product. The film was stretched by an external force along the long axis direction to 1.5-1.8 times the original length, and fixed (FIG. 4d). The film was placed in a vacuum oven at 120° C. and reacted for 48 h to complete the second crosslinking (FIG. 4e). After the reaction, the film was cooled to room temperature, to obtain a corresponding fluorine-containing liquid crystal elastomer film (FIG. 4f). FIG. 4 shows a flow chart of a preparation process above. In FIG. 4f, the dots represent the NIR cross-linked points in the liquid crystal elastomer film, and the line between the cross-linked points represents the fluorine-containing liquid crystal polymer.

Figure 5:
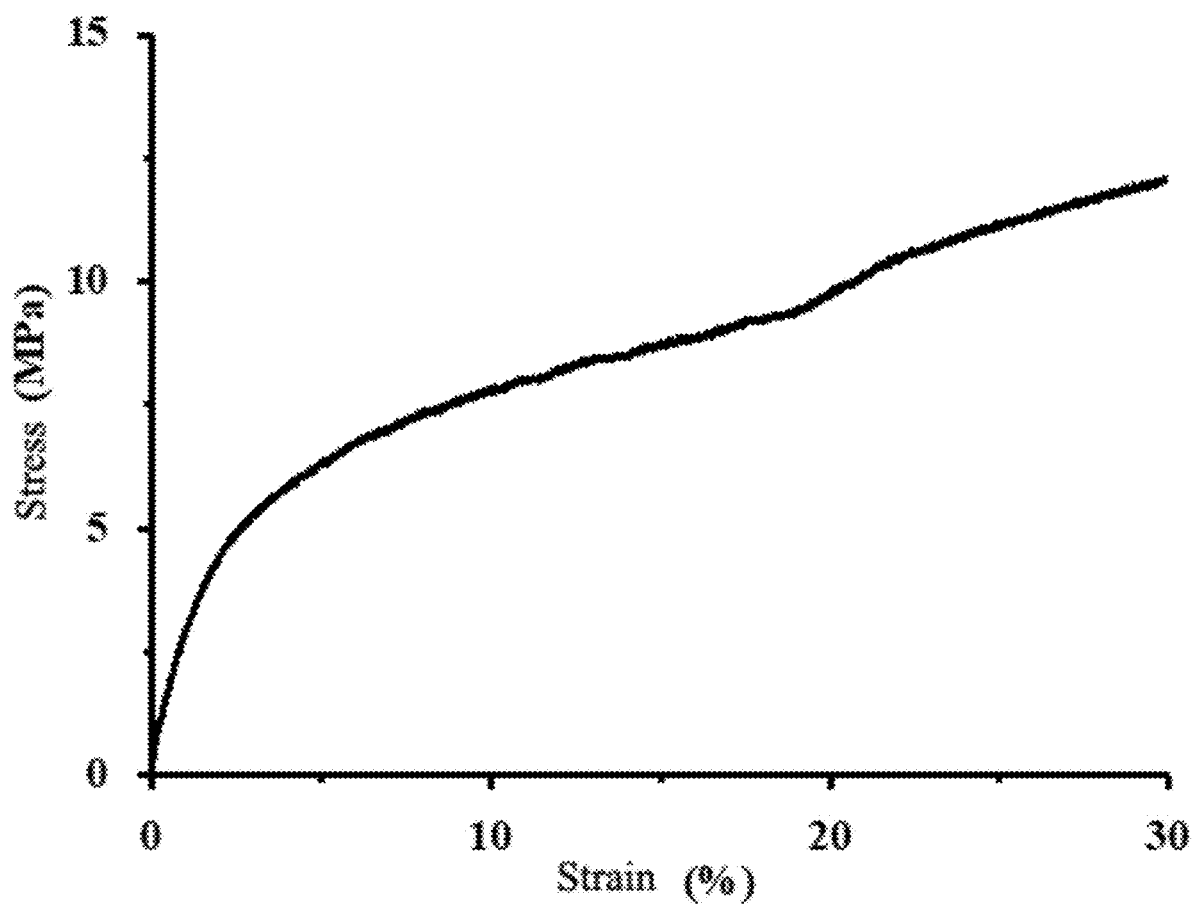
FIG. 5 shows a stress-strain curve of a fluorine-containing liquid crystal elastomer prepared in Example 3.
Figure 6:
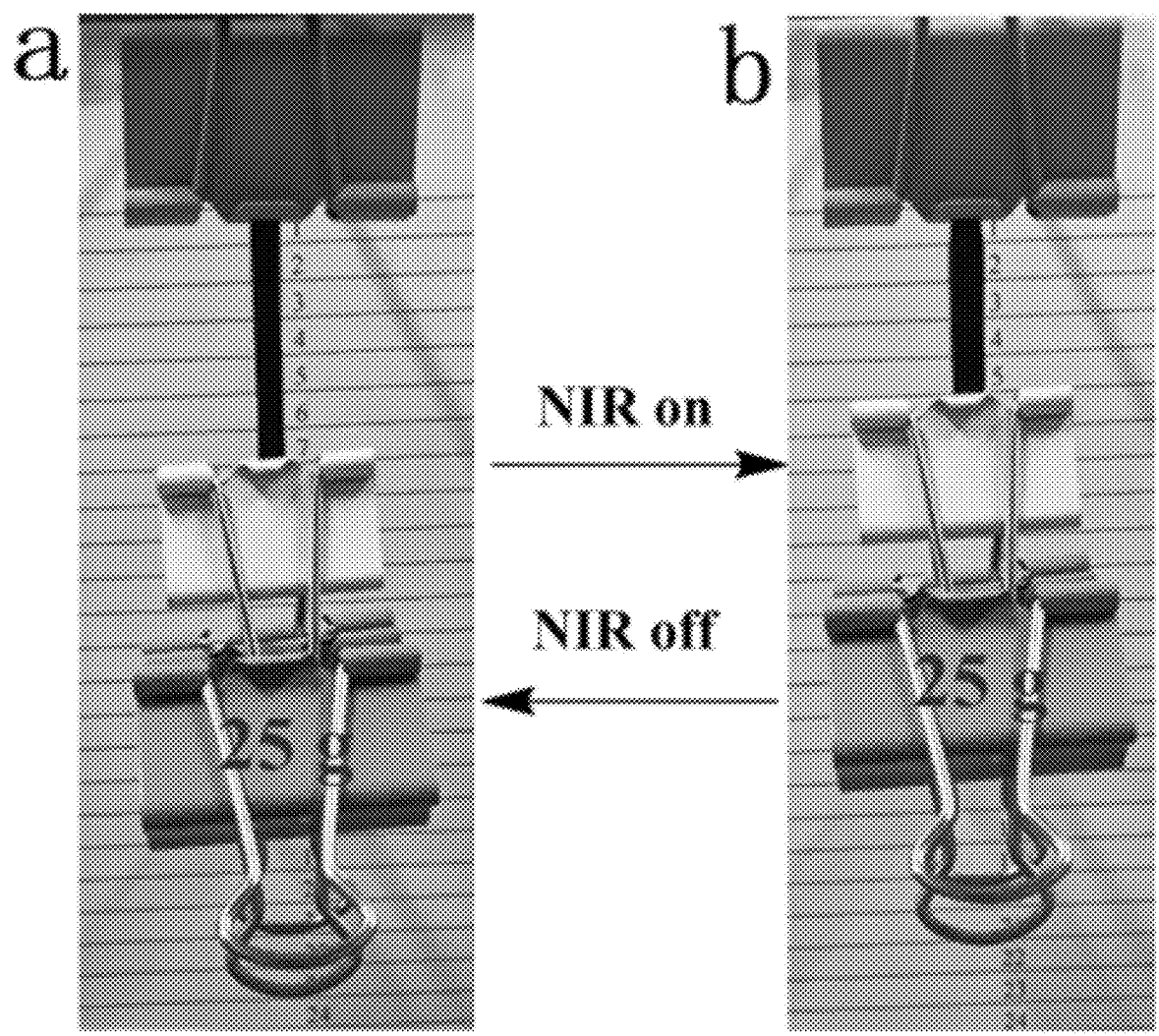
FIG. 6 shows the fluorine-containing liquid crystal elastomer prepared in Example 3 pulled by a weight of 25 g under light irradiation (1.50 W·cm$^{-2}$, 825 nm)
Figure 7:
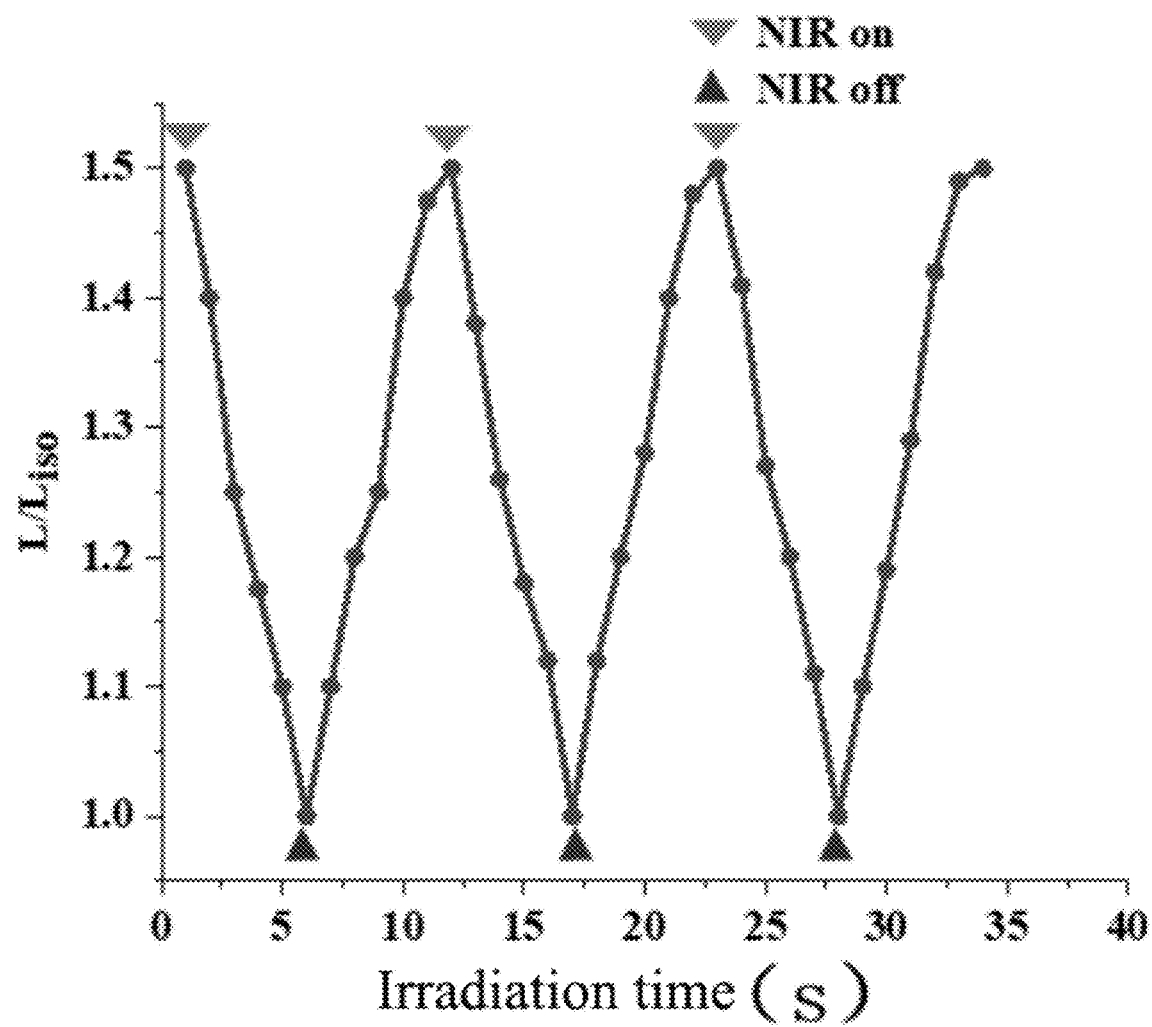
FIG. 7 shows the change in film length of the fluorine-containing liquid crystal elastomer prepared in Example 3 over time of irradiation.

The Young's modulus of the fluorine-containing liquid crystal elastomer film was tested (as shown in FIG. 5). The Young's modulus of the elastomer is as high as 216.63 MPa, which is much higher than that of general liquid crystal elastomers. In addition, the performance of the material is also characterized by physical test in the present invention. As shown in FIG. 6, a weight of 25 grams was suspended under the film. The weight was pulled up under light irradiation (1.50 W·cm$^{-2}$, 825 nm) (FIG. 6a). Then the light was turned off, and the weight was put down (FIG. 6b). The above process can be performed cyclically. As shown in FIG. 7, L represents the real-time length of the liquid crystal elastomer film, $L_{iso}$ represents the length of the liquid crystal elastomer film when it is isotropic, that is, the minimum length at room temperature, "NIR on" represents the light-on point, and "NIR off" represents the light-off point. Unless otherwise specified, the meanings are applicable in the following drawings. FIG. 7 shows that after repeated cycles of light on-off, the elasticity of the liquid crystal elastomer film remains basically unchanged under load conditions, which indicates that it has excellent light response behavior and good mechanical properties.

Example 4: Near-Infrared Light-Controlled Liquid Transport Pump

Figure 8:
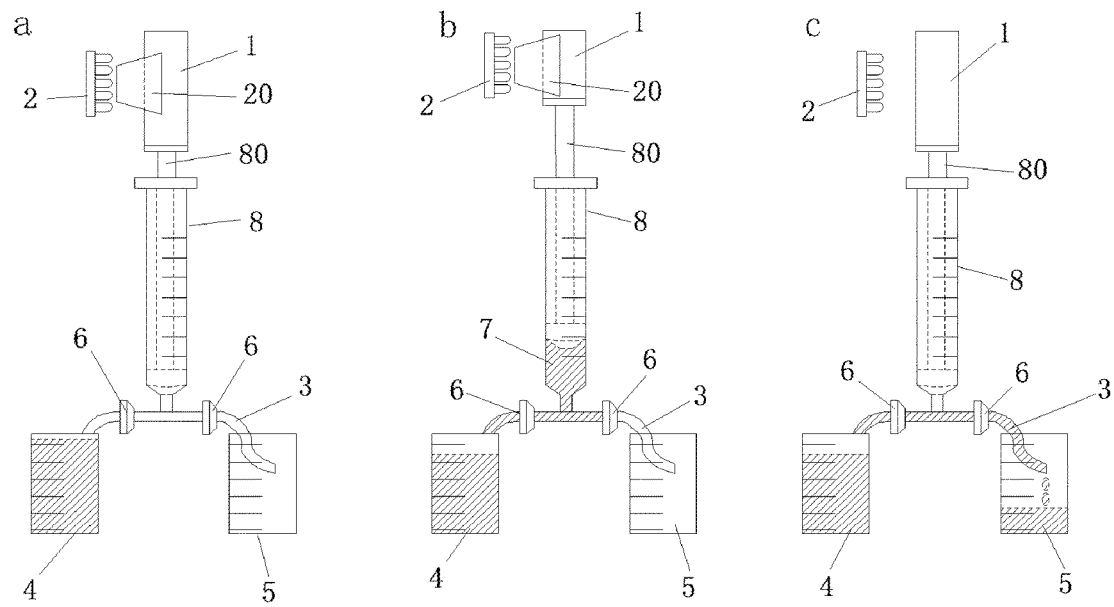
FIG. 8 is a schematic view showing the structure of a near-infrared light controlled liquid transport pump.

Based on the working principle of reciprocating piston pumps, the present invention also designs a liquid transport device that is absolutely controlled by near-infrared light to realize fast and constant quantitative liquid transport under control by light. The schematic structural view is shown in FIG. 8.

Figure 9:
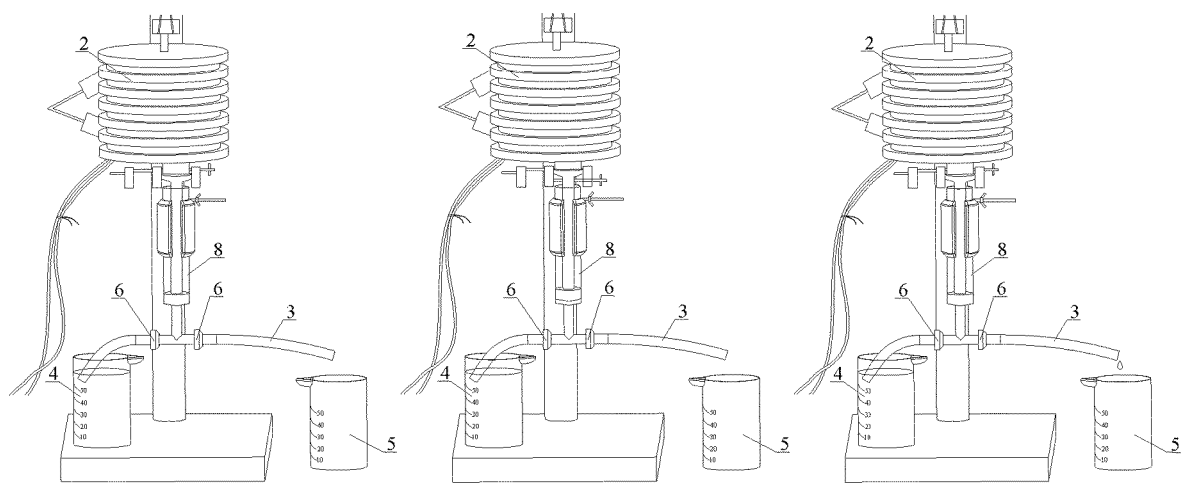
FIG. 9 is a physical picture of a near-infrared light controlled liquid transport pump.

The near-infrared light-controlled liquid transport pump includes a fluorine-containing liquid crystal elastomer 1 of the present invention, a light source 2 for generating near-infrared light 20 and irradiating the fluorine-containing liquid crystal elastomer 1, and a liquid delivery pipe 3 for liquid delivery. The shape of the light source 2 in FIG. 8 can be set as required to ensure that the near-infrared light 20 emitted is irradiated to the surface of the fluorine-containing liquid crystal elastomer 1. Preferably, the light source is circular (as shown in FIG. 9), and the fluorine-containing liquid crystal elastomer 1 is positioned in the center. Two ends of the liquid delivery pipe 3 are respectively in fluid communication with a first container 4 and a second container 5, where the first container 4 and the second container 5 are used to hold a liquid. The liquid delivery pipe 3 is also connected with a water storage unit 7, and the water storage unit 7 is preferably a syringe that is respectively in fluid communication with the first container 4 and the second container 5. The syringe is provided with a piston rod 80 therein, and the piston rod 80 is connected with the fluorine-containing liquid crystal elastomer 1. A one-way valve 6 is provided respectively between the first container 4 and the water storage unit 7 and between the second container 5 and the water storage unit 7. By controlling the on or off of the light source 2, the fluorine-containing liquid crystal elastomer 1 is allowed to shrink and recover to drive the piston rod 80 to reciprocate, whereby the piston rod 80 drives the liquid in the first container 4 to flow from the first container 4 to enter the second container 5 via the water storage unit 7.

When the light source 2 is turned on, the fluorine-containing liquid crystal elastomer 1 shrinks and the piston rod 80 is driven to move, so that the liquid in the first container 4 is sucked into the water storage unit 7 via the one-way valve 6 on the liquid delivery pipe 3. When the light source 2 is turned off, the fluorine-containing liquid crystal elastomer 1 gradually recovers to the original length, and the piston rod 80 is driven to move, so that the liquid in the water storage unit 7 is delivered to the second container 5 through the liquid delivery pipe 3. Because a one-way valve 6 is provided respectively between the first container 4 and the water storage unit 7 and between the second container 5 and the water storage unit 7, the liquid will not flow into the first container 4 again. FIGS. 8a, b, and c illustrate the entire transport process of a liquid in the liquid transport pump controlled by the near-infrared light 20.

In the near-infrared light-controlled liquid transport pump, the light response speed of the material can be improved by increasing the proportion of the near-infrared dye in the elastomer or increasing the power of the near-infrared light, thereby increasing the liquid transport rate. As the proportion of the near-infrared dye or the power of the light source 2 increases, the mechanical performance of the material is affected to a certain extent, and the mechanical performance of the material directly determine the service life of the light controlled device. Therefore, light sources 2 of different intensities can be used according to different work requirements.

Figure 10:
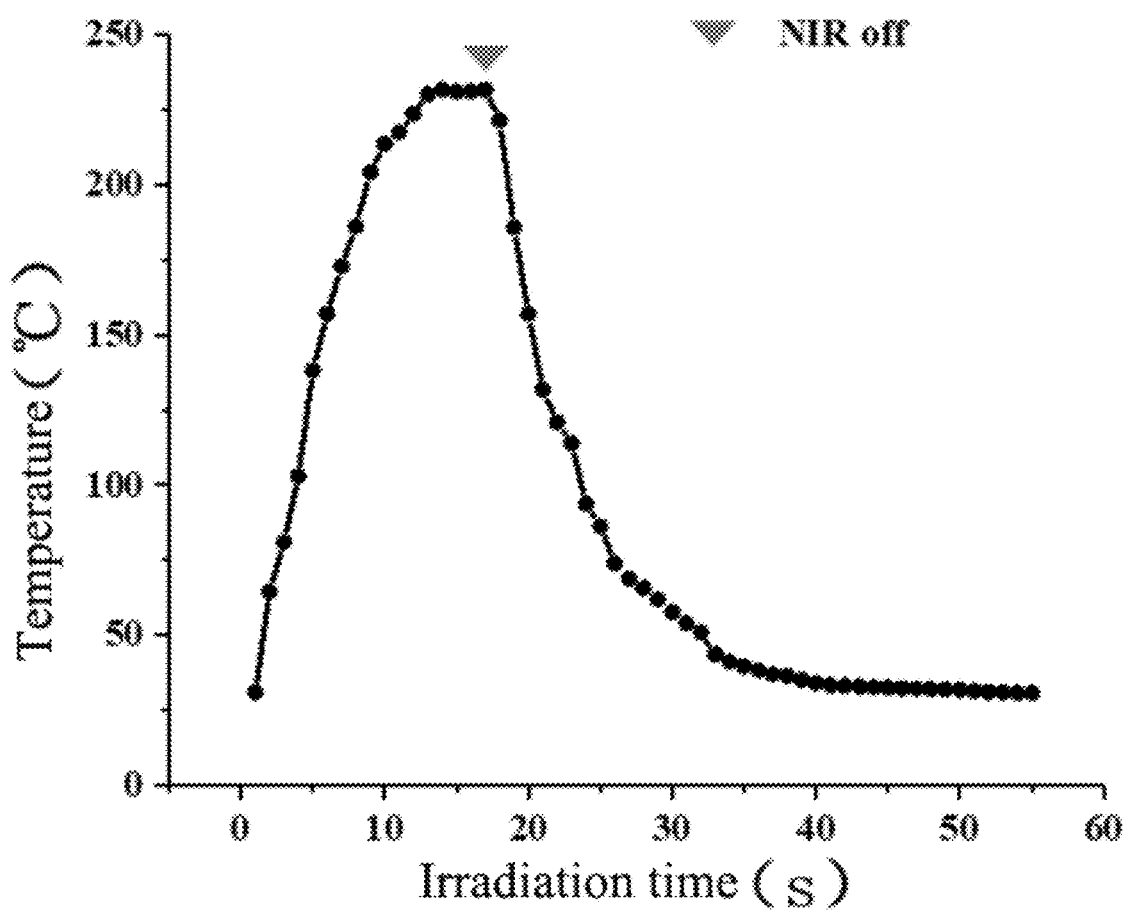
FIG. 10 is a curve showing the change in temperature at the surface of a fluorine-containing liquid crystal elastomer in a near-infrared light controlled liquid transport pump over time of irradiation (0.65 W·cm$^{-2}$, 825 nm)
Figure 11:
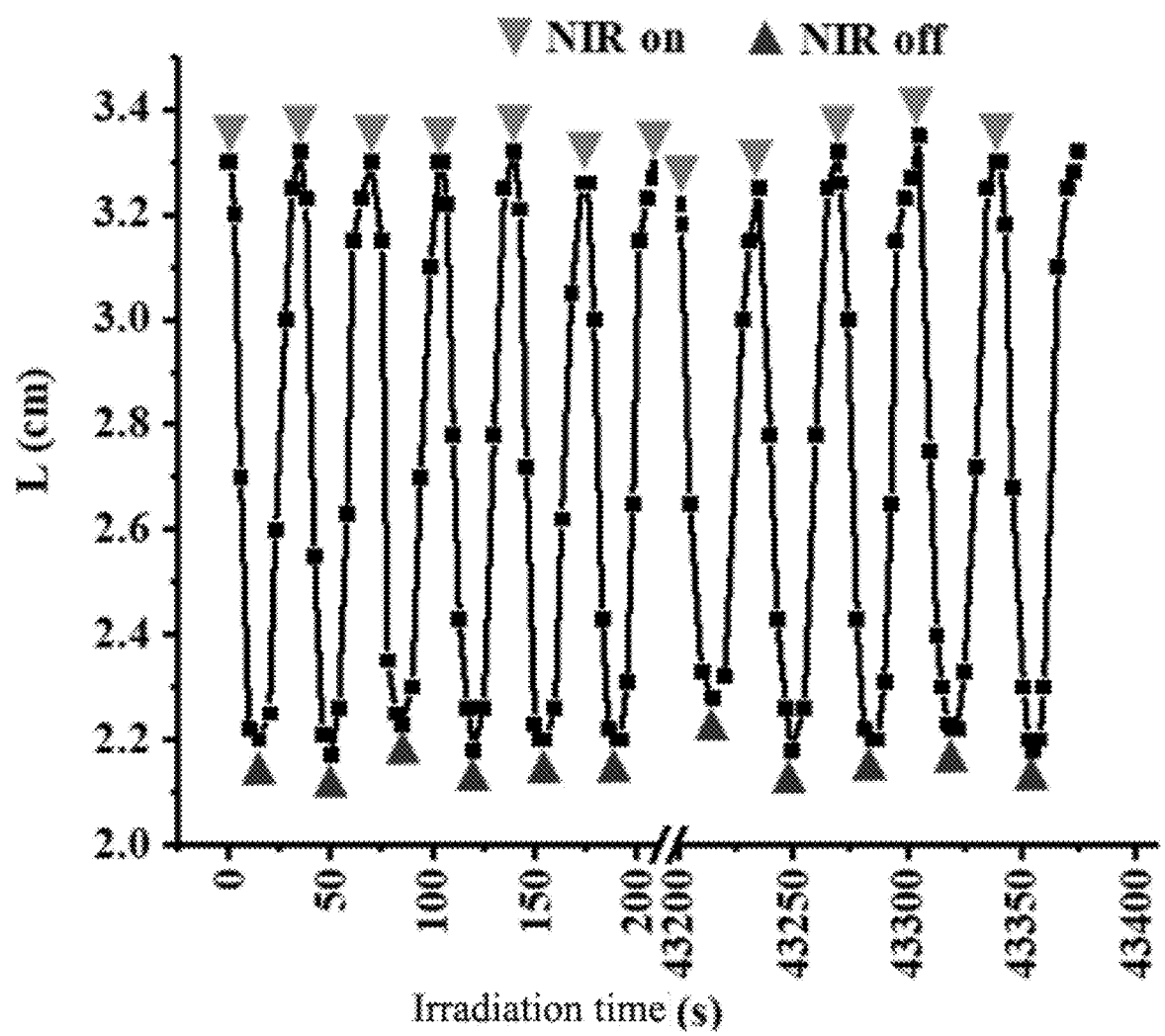
FIG. 11 is a curve showing the change in length of a fluorine-containing liquid crystal elastomer film in a near-infrared light controlled liquid transport pump over time of irradiation.

To be more suitable for practical use and take into account the response rate and service life, the mass fraction of the near-infrared dye is controlled to 8.93%, and the power of the light source 2 is controlled to 0.65 W·cm$^{-2}$ in the present invention. The physical diagram of the equipment is shown in FIG. 9. FIGS. 9a, b, and c are respectively physical diagrams of the equipment at the times when the light source 2 is just turned on, the light source 2 is just turned off after 15 s of light on, and the light source 2 is being turned off for 20 s, and the equipment in the Figs. works continuously for more than 12 h. In FIG. 9, the distance between two dotted lines marked on the syringe is the height difference of the liquid levels in the syringe. In FIG. 9, the first container 4 and the second container 5 are both beakers. The mass fraction of the near-infrared dye is controlled to 8.93% based on the weight of the fluorine-containing liquid crystal elastomer 1 as a film (the final product of Example 3). Under the light source 2 of such a power, it takes 15 seconds for the temperature on the film surface to reach the maximum value, and it takes 20 seconds to return to room temperature, as shown in FIG. 10. Based on this, the working period of the near-infrared light controlled liquid transport pump is set to 35 seconds in the present invention. In addition, the cyclic work period of the equipment needs to be stable, because the switching period of the light source 2 can only be set under a stable cyclic work period, to achieve fully automatic transport. The actual work period of the near-infrared light controlled liquid transport pump is the same as that designed in the present invention, and the cyclic work period is 35 seconds, where the light-on state lasts for 15 seconds and the light-off state lasts for 20 seconds. In the light-on state, the liquid crystal elastomer film shrinks to suck the liquid into the syringe; and in the light-off state, the liquid crystal elastomer film is recovered to transport the liquid to other places. To verify the working stability of the device, the real-time length of the fluorine-containing liquid crystal elastomer 1 as a film in the device over time of irradiation is recorded in real time. As shown in FIG. 11, it can be concluded from the experimental data that under the light source 2 having an intensity of 0.65 W·cm$^{-2}$, the device can work continuously for at least 12 h, which fully meets the requirements of practical applications.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for preparing a fluorine-containing liquid crystal elastomer, comprising steps of:
   (1) under a protective atmosphere, reacting a fluorine-containing liquid crystal polymer of Formula (1) and a near-infrared dye of Formula (2) in the presence of Grubbs catalyst in an organic solvent at 58-65° C. for 1.5-2.5 h to obtain a preliminarily cross-linked polymer; and
   (2) applying an external force to the preliminarily cross-linked polymer, and allowing the preliminarily cross-linked polymer to react at 110-130° C. under the action of the external force, to obtain the fluorine-containing liquid crystal elastomer after the reaction is completed, wherein the compounds of Formulas (1)-(2) are shown below:

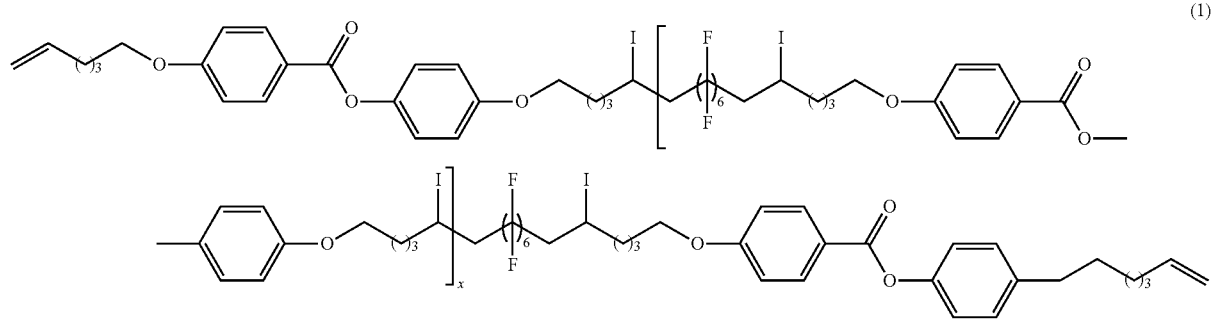

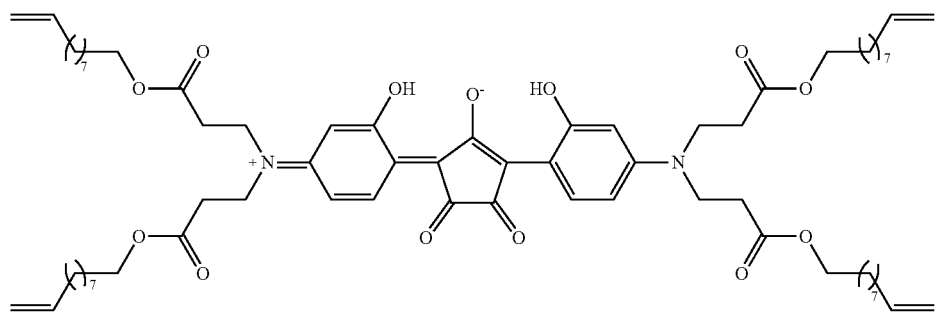

(2)

where X=5-12.

2. The method for preparing a fluorine-containing liquid crystal elastomer according to claim 1, wherein in Step (1), the molar ratio of the fluorine-containing liquid crystal polymer to the near-infrared dye is 4:1-6:1.

3. The method for preparing a fluorine-containing liquid crystal elastomer according to claim 1, wherein in Step (1), the preliminarily cross-linked polymer is in the shape of a film; and in Step (2), the external force is a tensile force, and the preliminarily cross-linked polymer in the shape of a film deforms along its length direction under the action of the external force.

4. The method for preparing a fluorine-containing liquid crystal elastomer according to claim 3, wherein under the action of the external force, the preliminarily cross-linked polymer in the shape of a film is extended to 1.5-1.8 times the original length.

* * * * *